United States Patent [19]
Soda et al.

[11] Patent Number: 5,861,154
[45] Date of Patent: *Jan. 19, 1999

[54] RECOMBINANT L-METHIONINE γ-LYASE

[75] Inventors: Kenji Soda, Uji; Hidehiko Tanaka, Okayama; Hiroyuki Inoue, Okayama; Manabu Sugimoto, Okayama; Kenji Inagaki, Okayama; Nobuyoshi Esaki, Otsu, all of Japan

[73] Assignee: Shionogi & Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 641,038

[22] Filed: Apr. 30, 1996

[30] Foreign Application Priority Data

Oct. 30, 1995 [JP] Japan .................................. 7-306672

[51] Int. Cl.⁶ .............................. A61K 38/51; C12N 9/88; C07H 21/04
[52] U.S. Cl. ........................ 424/94.5; 435/232; 536/23.2
[58] Field of Search .......................... 435/232; 424/94.5; 536/23.2

[56] References Cited

FOREIGN PATENT DOCUMENTS

| | | |
|---|---|---|
| WO95/17908 | 7/1995 | WIPO . |
| WO95/18233 | 7/1995 | WIPO . |
| WO94/11535 | 5/1996 | WIPO . |

OTHER PUBLICATIONS

Nakayama et al.(Jul. 1984) Purification of Bacterial L–Methionine gamma–Lyase Analytical Biochemistry 138: 421–424.

Erickson et al. (Jul. 1990) Sequence of cDNA for rat cystathionine gamma–lyase and comparison of deduced amino acid sequence with related *Escherichia coli* enzymes, Biochemical Journal 269: 335–340.

Rudinger, J. (Jun. 1976) Characteristics of the amino acids as components of a peptide hormone sequence, In Peptide Hormones, Ed. J. A. Parsons, University Park Press, pp. 1–7.

Ngo et al. (Jan. 1994) Computational complexity, protein structure prediction, and the ILevinthal paradox. In: The Protein Folding Problem and Tertiary Structure Prediction. Eds. Merz et al. Birkhauser et al. Boston, Ma. pp. 491–495.

Thornton et al. (Sep. 1995) Protein Engineering: Editorial Overview. Current Opinion in Biotechnology 6(4): 367–369.

Wallace (Apr. 1993) Understanding cytochrome c function: engineering protein structure by semisynthesis. The FASEB Journal 7: 505–515.

JB vol. 117, No. 5 May 1995, "The Journal of Biochemistry".

Nakayama et al, Biochemistry, 27, pp. 1587–1591 (1988).

Lishko et al, Protein Expression and Purification, 4, pp. 529–533 (1993).

Nippon Nogeikagaku Kaisha, 68, p. 106 (Mar. 3, 1994).

*Primary Examiner*—Robert A. Wax
*Assistant Examiner*—Einar Stole
*Attorney, Agent, or Firm*—Birch, Stewart Kolasch & Birch, LLP

[57] ABSTRACT

A recombinant protein capable of constituting a recombinant L-methionine γ-lyase or a variant thereof, a recombinant oligomeric enzyme, preferably tetrameric enzyme, consisting of the recombinant protein, a DNA molecule encoding the same, an expression vector containing the DNA molecule, a host cell harboring the expression vector, a method of preparing the recombinant L-methionine γ-lyase, and anti-tumor agent comprising the recombinant L-methionine γ-lyase or a variant thereof are provided.

9 Claims, 3 Drawing Sheets

FIG. 1

Met-His-Gly-Ser-Asn-Lys-Leu-Pro-Gly-Phe-Ala-Thr-Arg-Ala-
Ile-His-His-Gly-Tyr-Asp-Pro probe : 5' GG(A/G) TC(A/G) TA(A/G/T/C) CC(A/G) TG(A/G) TG(A/G/T) AT 3'  20 bases (combination: 192 Kinds)

RECOMBINANT L-METHIONINE γ-LYASE

FIELD OF THE INVENTION

The present invention relates to a recombinant L-methionine γ-lyase. More particularly, it relates to a recombinant protein capable of constituting a recombinant L-methionine γ-lyase or a variant thereof, a recombinant oligomeric enzyme consisting of the recombinant protein or its variant, a DNA molecule encoding the same, an expression vector containing the DNA molecule, a host cell harboring the expression vector, a method of preparing the recombinant L-methionine γ-lyase of the present invention by culturing the host cell, and anti-tumor agent comprising the recombinant L-methionine γ-lyase or a variant thereof.

BACKGROUND OF THE INVENTION

L-methionine γ-lyase (EC 4.4.1.11) is an enzyme which requires pyridoxal phosphate as a co-enzyme and catalyzes α, γ-elimination and γ-replacement of L-methionine or its derivatives and also α, β-elimination and β-replacement of S-substituted L-cysteine or its derivatives [Tanaka, H. et al., Biochemistry, 16, 100–106 (1977)]. This enzyme has been isolated and purified mainly from *Pseudomonas putida* and its physicochemical and enzymological properties have already been shown [Nakayama, T. et al., Anal. Biochem., 138, 421–424 (1984)]. There have been some researches reporting the mechanism of enzymatic reaction catalyzed by L-methionine γ-lyase [Esaki, N. et al., FEBS Lett., 84, 309–312 (1977); Nakayama, T. et al., Biochemistry, 27, 1587–1591 (1988), and the like]. The references which have been provided so far are all related to L-methionine γ-lyases purified from natural source such as bacteria belonging to genus Pseudomonas. Thus, there are no references describing or suggesting the preparation of a recombinant enzyme by means of genetic engineering.

Recently, it has been suggested that naturally occurring L-methionine γ-lyase purified from a culture of *P. putida* may have an anti-tumor activity [WO94/11535, Publication date, May 26, 1994).

To develop a therapeutically applicable and useful drug, a substance to be used as an active ingredient should be pure or essentially free from undesirable contaminants, for example, proteins or the like by which the substance is naturally accompanied, and can be produced on a large scale so as to meet the demands. Accordingly, the establishment of a method of preparing L-methionine γ-lyase or its variants with essentially the same enzymatic activity by means of recombinant DNA technique must contribute to the development of useful anti-tumor agents.

WO95/17908 has revealed production of L-methionine γ-lyase using gene recombinant technique, and describes the DNA sequence and the deduced amino acid sequence L-methionine γ-lyase. However, the document shows neither any primers for isolating the DNA encoding L-methionine γ-lyase nor any source from which the DNA comes.

SUMMARY OF THE INVENTION

The present inventors have succeeded in isolating and identifying DNA encoding L-methionine γ-lyase from a strain of *Pseudomonas putida*, cloning and expression of the same in *Escherichia coli* and preparing the recombinant enzyme using the same.

The enzyme L-methionine γ-lyase is known to be an oligomeric enzyme. As will be described in detail below, four units of the recombinant protein of the present invention, when it is produced in a recombinant strain transformed with an expression vector containing a DNA encoding the said protein, combine spontaneously to form the oligomeric enzyme with L-methionine γ-lyase activity. Thus, the protein of the present invention having amino acid sequence shown in SEQ ID NO:1, although it does not have any biological activity by itself, is a subunit of L-methionine γ-lyase which is expected to be useful as anti-tumor agent as mentioned above.

Accordingly, in the present specification, the terms "recombinant L-methionine γ-lyase" and "recombinant protein" encoded by DNA having nucleotide sequence shown in SEQ ID NO: 1 and a derivative thereof capable of constituting oligomeric enzyme having L-methionine γ-lyase activity may be used exchangeably.

DETAILED DESCRIPTION OF THE INVENTION

One of strains of *P. putida* capable of providing a DNA encoding a protein constituting a recombinant L-methionine γ-lyase of the present invention, *P. putida* ICR 346 has been deposited at the "National Institute of Bioscience and Human-Technology, Agency of Industrial Science and Technology", at Higashi 1-1-3, Tsukuba-shi, Ibaraki-ken, Japan under the Budapest Treaty (accession number: FERM BP-5238; deposition date: Sep. 25, 1995). The mycological characteristics of *Pseudomonas putida* ICR 3460 are shown below.

1. Morphology

It is a Gram-negative aerobic rods motile by one or several polar flagella, and dose not grow under anaerobic conditions. Its size ranges 0.7 to 1.0 μm in diameter and 2.0 to 3.5 μm in length.

2. Characteristics of Culture (1) Nutrient agar plate culture (at 30° C. for 24 to 168 hours)

Growth rate: Colonies were formed after 24 hours.

Form: Circular

Surface: Smooth

Margin: Entire

Elevation: Raised

Chromogenesis: Pale yellow

Lustre: Glistening

Optical characters: Opaque (2) Nutrient agar slant culture (at 30° C. for 24 to 168 hours)

Growth: Abundant

Form of growth: Spreading

Surface: Smooth

Chromogenesis: Pale yellow

Lustre: Glistening

Optical characters: Opaque

Consistency: Butyrous (3) Nutrient broth liquid culture (at 30° C. for 24 to 168 hours)

Surface growth: Membranous

Clouding: Moderate

Odor: Decided

Sediment: Compact

Amount of sediment: Abundant

3. Biochemical Properties (1) Nitrate reduction: Negative (2) Methyl red test: Negative (3) Voges-Proskauer test: Negative
(4) Indole production: Negative
(5) $H_2S$ production: Negative
(6) Starch hydrolysis: Negative
(7) Citrate utilization: Positive
(8) Production of pigment: Water-soluble fluorescent yellow-green pigment was produced.
(9) Urease: Negative
(10) Oxidase: Positive
(11) Catalase: Positive
(12) OF-test: Sugars were decomposed by oxidation.
(13) Utilization of carbon compounds
 i) D-Glucose: Positive
 ii) L-Arabinose: Negative
 iii) D-Mannose: Negative
 iv) D-Mannitol: Negative
 v) Maltose: Negative
 vi) N-Acetylglucosamine: Negative
 vii) Potassium gluconate: Positive
 viii) N-Capric acid: Positive
 ix) Adipic acid: Negative
 x) DL-Malic acid: Positive
 xi) Phenylacetate: Positive
(14) Arginine dihydrolase: Positive
(15) Esculin hydrolysis: Negative
(16) Gelatin liquefaction (hydrolysis): Negative
(17) Deoxyribonuclease (DNase): Negative
(18) β-Galactosidase (PNPG test): Negative
(19) Acylamidase: Negative
(20) Growth under anaerobic conditions: Negative
(21) Behavior for oxygen: Aerobic The bacterial strain was identified as a strain of *Pseudomonas putida* by comparing its taxonomic properties with the taxonomic description about *P. putida* in Bergey's Manual of Systematic Bacteriology Vol. 1 (1984), and designated as *Pseudomonas putida* ICR 3460.

The present invention also provides a method of preparing recombinant L-methionine γ-lyase, which comprises constructing a recombinant vector by introducing a DNA sequence encoding the amino acid sequence shown in SEQ ID No. 1 into a vector used in the host/vector system for expression in *E. coli*, transforming an *E. coli* host cell with the vector, and culturing the transformant. The present method can be carried out according to the steps as exemplified below. As is easily understood by one ordinary skilled in the art, once the DNA sequence coding L-methionine γ-lyase is disclosed by the present invention, certain steps can be omitted or simplified.

(1) A strain of *P. putida* is grown overnight at 28° C. in a suitable medium. Example of medium includes those obtainable by adding L-methionine to a conventional medium in which a species of Pseudomonas can generally grow. From the resulting culture broth, cells are harvested and mechanically disrupted. After the cell debris was discarded by centrifugation, the supernatant is subjected to dialysis followed by ion exchange chromatography (2 times) and the like to purify L-methionine γ-lyase. The purified L-methionine γ-lyase is digested with a suitable chemical reagent or enzyme generally used for fragmentation of protein. Peptide fragments are separated into respective ones and one of them is subjected to the amino acid sequencing from the amino terminus.

(2) A base sequence of a DNA capable of encoding a portion of the amino acid sequence of the peptide fragment of the purified L-methionine γ-lyase protein is deduced. Oligonucleotides corresponding to the deduced base sequences are chemically synthesized, labeled at its 5'-terminus with $^{32}P$ and used as a probe for gene cloning.

(3) The chromosomal DNA is extracted from *P. putida*, digested with an appropriate restriction endonuclease and subjected to electrophoresis on agarose gel. The relevant region on the agarose gel containing the DNA fragment encoding L-methionine γ-lyase protein is excided and the DNA is extracted.

(4) The DNA obtained in the step (3) is inserted into a cloning vector for *E. coli* and the resultant recombinant vector is intorduced into a strain of *E. coli*, for example *E. coli* strain MV1184, JM109 or the like. The transformant is cultured so as to form colonies or plaques on an agar medium. Then, colony or plaque hybridization is carried out using the $^{32}P$ labeled probe, and the colony or plaque showing homology with the probe is selected and isolated.

(5) The recombinant plasmid is extracted from the selected *E. coli* strain or phage particles. After the restriction enzyme map is prepared, the base sequence of the cloned DNA fragment derived from *P. putida* is determined. The amino acid sequence deduced from thus determined DNA base sequence is compared with known partial amino acid sequences, terminal amino acid sequence and amino acid composition of L-methionine γ-lyase. Finally, the base sequence of the structural gene of L-methionine γ-lyase is determined.

(6) An expression plasmid is constructed by inserting the structural gene of L-methionine γ-lyase into an expression vector for *E. coli* so that the gene is located downstream from an *E. coli* promoter.

(7) The expression plasmid is then introduced into *E. coli* host cells to obtain novel *E. coli* transformants capable of producing L-methionine γ-lyase.

One ordinary skilled in the art can easily carry out general operations required for handling DNA in the above steps in accordance with the experimental mannals, for example, "Molecular Cloning" 2nd edition [Sambrook, J. et al., Cold Spring Harbor Laboratory (1989)]. All the enzymes, reagents and the like used in the above steps are commercially available. Unless otherwise noted, one can achieve the purpose completely just by using them under the conditions as instructed by the manufacturers.

In the step (1), the method of amino acid sequencing is known and can be carried out by means of, for example, a commercially available automatic amino acid sequencer. In the step (2), oligonucleotides having an intended base sequence can be synthesized by the use of a commercially available DNA synthesizer according to the indicated operation procedures. In the step (5), the DNA sequencing can be carried out according to the known method of Sanger et al., Proc. Natl. Acad. Sci. U.S.A., 74, 5463–5467 (1977), using M13 vector system.

Example of *E. coli* vectors used for cloning in the step (4) includes plasmid vectors such as pUC118, pUC119, pUC13, pBR322, pAT153 and the like and phage vectors such as λZAPII, λgt10 and the like.

Example of *E. coli* strains usable as a host for cloning and expression includes strains of *E. coli* K-12 such as HB101, DH1, C600, JM103, JM105, JM109, MV1184 and the like. The above-mentioned vectors and hosts are marketed and available in ease.

When yeast is used as a host for expression, the objective recombinant L-methionine γ-lyase can be separated from the supernatant of culture broth easily. In this case, vectors such as pYES2, pYEUra3 and the like can be used. It is possible to carry out so-called self-cloning by the use of a strain of genus Pseudomonas bacteria as a host. In this case, vectors such as RSF1010, RK2 and the like are used.

In the step (6), a plasmid capable of directing an efficient expression of a gene of interest in E. coli can be constructed by inserting a DNA fragment containing the intended structural gene of L-methionine γ-lyase into an expression vector such as pKK223-3, pPL-lambda or the like which comprise suitable promoters (e.g., Lac, Tac, Trp, $\lambda P_L$ or the like) functional in the host together with Shine-Dalgarno (SD) sequence, or ATG vector such as pKK233-2, pTrc99A or the like which further comprises the translational initiation codon ATG. An efficient expression can be achieved by introducing the resultant expression plasmid into a suitable host such as E. coli strain JM103, JM109, HB101, C600 or the like.

The expression product, L-methionine γ-lyase, can be purified using conventional methods including centrifugation, gel filtration, ion exchange chromatography and the like, alone or in an appropriate combination.

The recombinant enzyme obtained by the present method has been proved to have L-methionine γ-lyase activity. It has also been confirmed that the activity is substantially unchanged even if methionine at the N-terminus of the amino acid sequence of the resultant recombinant L-methionine γ-lyase is absent.

As used herein, the term "variants of recombinant proteins" refers to proteins feasible to either chemical or biochemical modification, or those having naturally or artificially modified amino acid or amino acid sequence, on condition that they have substantially the same functions or activity as those of the recombinant protein of the present invention having amino acid sequence shown in SEQ ID NO: 1. Such variants can be prepared by methods well known in the art, for example, site-directed mutagenesis by PCR method and the like.

The variants are exemplified by proteins in which the amino acid sequence is slightly different from No. 2 to No. 398 of that shown in SEQ ID NO: 1, induced by minor alteration such as addition, deletion and/or substitution of an amino acid or an amino acid sequence and which have substantially the same functions or activities as those of the recombinant protein of the present invention comprising the amino acid sequence from No. 2 to No. 398 of the shown in SEQ ID NO:1. Preferably, such variants include the proteins shich contain one or more alteration(s) as shown above of one or a few amino acid(s). More preferably, the variants include proteins having 85% or more homology in the amino acid sequence to the recombinant protein of the present invention.

The present invention also provides DNA molecules encoding such variants. Preferably, the DNA molecules include the nucleotide sequences which encode the variants and which are analogous to that of No. 64 to No. 1254 of that shown in SEQ ID NO;1.

As will be understood from the specification, when a strain of E. coli transformed with an expression vector of the present invention is grown in an appropriate medium, the expressed recombinant protein in solubilized fraction (cell-free extract) by itself forms the oligomer, thereby providing a biologically active recombinant enzyme. The resultant oligomer, preferably tetramer of the recombinant protein of the present invention or a variant thereof is useful as an anti-tumor agents [see, WO94/11535].

Accordingly, the present invention further provides an anti-tumor agent comprising the recombinant L-methionine γ-lyase of the present invention or variants thereof. The anti-tumor agent of the present invention can be prepared using any of known carriers or excipients therefor. It is typically in the form of injections and can be lyophilized products. For administration, it will be generally infused parenterally every day over several ten minutes to several hours for several days to several weeks. Although the administration dose varies depending on intended effects, sex, age, weight and severity of symptoms of patients and the like, it is generally from about 1 to 1000 U/kg weight/day, and preferably from about 50 to 500 U/kg weight/day.

BRIEF EXPLANATION OF DRAWINGS

FIG. 1 shows the N-terminal amino acid sequence of native L-methionine γ-lyase purified from P. putida, wherein the partial sequence used for preparation of oligonucleotide probes used in the isolation of DNA encoding L-methionine γ-lyase is underlined. It is also shown nucleotide sequences which can encode the partial amino acid sequence and is usable as oligonucleotide probes.

Figure 2:
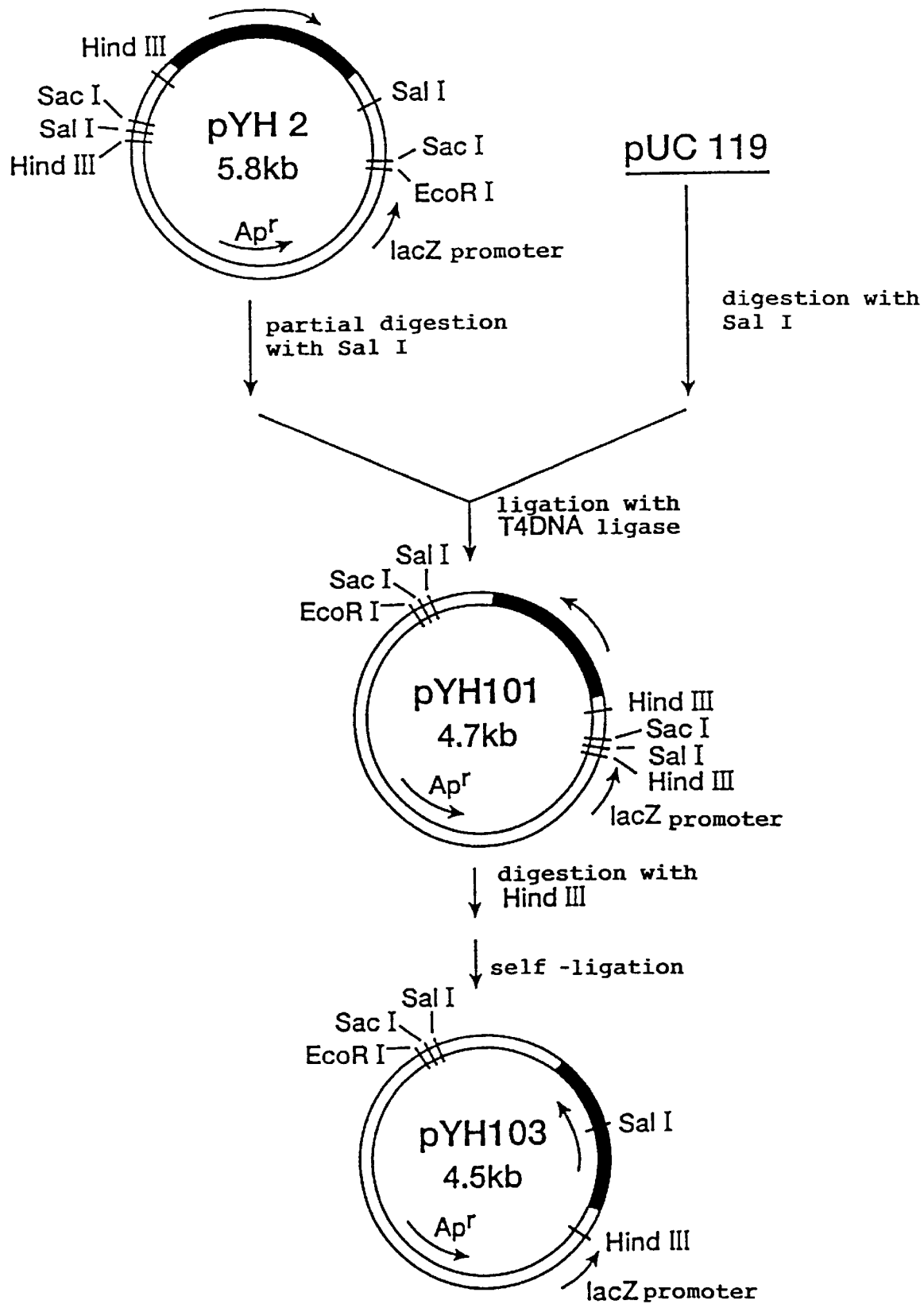
FIG. 2 is a flow chart illustrating the procedures for constructing the expression plasmid pYH103.

The following Examples further illustrate the present invention in detail but are not to be construed to limit the scope thereof.

Unless otherwise stated, throughout the Examples below, the digestion reaction using a restriction endonuclease was carried out at 37° C. for 2 hours in an indicated buffer according to the instructions of the manufacturers.

Further, the ligation reaction using T4 DNA ligase was carried out at 16° C. for 16 hours in an indicated buffer according to the instructions of the manufacturer.

Transformation of E. coli with a plasmid was carried out according to the method of Cohen et al. (Cohen et al., Proc. Natl. Acad. Sci. USA, 69, 2110–2114 (1972)).

Example 1

Synthesis of DNA Probes and End-Labeling

Pseudomonas putida was grown at 28° C. in an L-methionine-containing production medium (0.25% L-methionine, 0.1% polypeptone, 0.1% glycerol, 0.1% $KH_2PO_4$, 0.1% $K_2HPO_4$, 0.01% $MgSO_4 \cdot 7H_2O$, 0.025% yeast extract, pH 7.2) according to the procedures described by Nakayama, T. et al, Anal. Biochem, 138., 421–424 (1984). Native L-methionine γ-lyase was purified from cells of P. putida according to the known procedures [Nakayama, T. et al, Anal. Biochem., 138, 421–424 (1984); and Nakayama, T. et al., Biochemistry, 27, 1587–1591 (1988)]. The purified enzyme was fragmented with cyanogen bromide and a fragment containing the N-terminal amino acid sequence was isolated and subjected to the determination of amino acid sequence by Edman's procedures using an automated amino acid analyzer. The amino acid sequence from residue 15 isoleucine to residue 21 proline from the N-terminus was as follows:

Ile His His Gly Tyr Asp Pro (SEQ ID NO: 3)

The sequence above has not been described in literatures.

The N-terminal amino acid sequence is shown in FIG. 1 together with nucleotide sequences which can encode a partial amino acid sequence indicated by underline, and be used a probe.

Thus, various oligonucleotides which can encode the amino acid sequence above were synthesized with a DNA synthesizer Model 391 (Applied Biosystems) as shown in FIG. 1. The DNA probe thus obtained was labeled at its 5' terminus using T4 polynucleotide kinase and [γ-$^{32}$P]ATP (220 TBq/mmol) [New Research Products] according to the known method [Maxam, A. M. and Gilbert, W., Methods Enzymol., 65, 499 (1980)].

Example 2

Cloning of DNA Fragment Encoding L-Methionine γ-Lyase Protein

1. Extraction of Chromosomal DNA from P. putida

P. putida ICR3460 (FERM BP-5238) was grown in LB medium overnight and cells were harvested from the culture (4 g, wet weight). After washing (2 times) with Nacl-EDTA (0.15M NaCl, 0.1M EDTA (pH 8.0)), the cells were suspended into Nacl-Tris (0.1M NaCl, 0.1M Tris-HCl (pH 9.0), 0.01M EDTA (pH 7.5)), and a portion (9 ml) of the suspension was placed in a rotor tube (30 ml capacity) to give about 1 g cells/tube. To the suspension was added 1 ml of 20 mg/ml lysozyme (Nacalai Tesgue) solution in Nacl-EDTA and the mixture was incubated at 37° C. for 20 minutes. After addition of 3 ml Tris-SDS [5% SDS in Nacl-Tris-EDTA (0.14M NaCl, 20 mM Tris-HCl (pH 7.5), 1 mM EDTA (pH 8.0))], the tube was gently inverted to suspend the mixture and then maintained at 60° C. for 20 minutes. After allowing the tube to cool to room temperature, 2.5 ml of 1.5 mg/ml proteinase K (Wako-Pure Chemical) was added and incubated for another 10 hours. To the mixture was added an equal volume of phenol solution (phenol saturated with 100 mM Tris-HCl (pH 8.0)) and the tube was allowed to stand for 30 minutes with occasional and gentle shaking, followed by centrifugation at 3000 rpm for 10 minutes. The contents in aqueous phase were combined in a flask containing cold ethanol. The precipitated DNA was wound around a glass stick, washed successively with 70%, 80%, and 90% ethanol, suspended in 20 ml 0.1x SSC (0.01M NaCl, 0.0015M sodium citrate). After the phenol treatment was repeated, 100 μl of 10 mg/ml RNaseA was added to the DNA solution and the mixture was incubated at 37° C. for 1 hour. After repeating the phenol treatment once more, the DNA was suspended in 15 ml NaCl-Tris-EDTA and centrifuged at 10,000 rpm for 10 minutes. The supernatant was dialyzed against TE buffer (10 mM Tris-HCl (pH 7.5)-1 mM EDTA (pH 8.0)) overnight. (The dialyzing tube had been treated by boiling in a mixture of 1 mM EDTA (pH 8.0) and 2% Na$_2$CO$_3$ for 10 minutes, washing with water and boiling again in 1 mM EDTA (pH 8.0) for 10 minutes). To the dialyzate was added 25 μl chloroform to obtain a DNA preparation. The purity of DNA was determined by calculating the ratio of absorbance at 260 nm to that at 280 nm. As a result, from 4 g (wet weight) cells was yielded 5 mg DNA in total.

To 80 μg of the DNA was added 560 units of restriction endonuclease PstI and reaction was carried out under an optimal condition. The resultant reaction mixture was electrophoresed on agarose gel in a conventional manner and subjected to Southern blot hybridization according to Southern's method [Southern, E. M., Methods Enzymol., 68, 152–176 (1979)] using the oligonucleotide probe end-labeled with $^{32}$P prepared in Example 1. The region of the gel corresponds to around 1 kb where the specific signal was detected was cut. The DNA fragments were extracted from the gel according to the method of Vogelstein and Gillespie, Proc. Natl. Acad. Sci. USA, 76, 615–619 (1979).

2. Cloning of PstI Fragment

Plasmid pUC118 (1.5 μg, Takara Shuzo) was digested with 120 units of restriction endonuclease PstI. To the reaction solution (2 μl) containing digested pUC118 were added 2 μg of a mixture containing PstI restriction fragments obtained in step 1 above and 1000 units of T4 DNA ligase (Nippon Gene) to ligate the PstI fragments into plasmid pUC118. The resultant mixture containing recombinant plasmids were used to transform E. coli MV 1184 (Takara Shuzo), and the transformants were spread over L-agar plate (1% polypeptone, 0.5% yeast extract, 1% NaCl, 1.5% agar) containing 50 μg/ml ampicillin and incubated overnight at 37° C. Colonies of transformants were transferred to nylon membrane (trade name; Hybond N+, Amersham) and the DNA derived from colonies were immobilized on the membrane according to a method well-known in the art.

Transformants were screened by colony hybridization using $^{32}$P-end-labeled oligonucleotide probes prepared in Example 1 (Hanahan et al., Gene, 10, 63–67, (1980)). As a result, one positive clone harboring the recombinant plasmid pMR1 was obtained.

The DNA base sequence analysis by the dideoxy chain termination method (Sanger et al., Proc. Natl. Acad. Sci. USA, 74, 5463–5467 (1977)) revealed that the plasmid pMR1 contains a 931 bp of PstI insert which contains only 422 bp fragment of the 5' terminal region of L-methionine γ-lyase gene.

3. Construction of Second Genomic Library

Prior to the re-cloning, an oligonucleotide probe corresponding to HindIII-PstI region containing 422 bp of 5' terminal region of L-methionine γ-lyase gene was prepared using plasmid pMR1 obtained in step 2 above as follows.

A 453 bp HindIII-PstI fragment was obtained from plasmid pMRI (30 μg) through the digestion with 300 units of restriction endonuclease HindIII, ethanol precipitation to terminate the reaction, and digestion with 300 units of restriction endonuclease PstI. The resultant DNA fragment was labeled with [α-$^{32}$P]dCTP (220 TBq/mmol; New Research Products) using random primer labeling kit (Takara Shuzo).

The chromosomal DNA was then extracted from P. putida ICR3460 (FERM BP-5238) in a manner similar to that described in step 1 above. The DNA (40 μg) was digested with 75 units of restriction endonuclease SacI and the resultant reaction mixture was electrophoresed on agarose gel in a conventional manner. Then, Southern blot hybridization was carried out using the end-labeled oligonucleotide probes obtained in step 3 above. The DNA fragment around 2.6 kb where the specific signal was detected was extracted from the gel.

Cloning phage vector λZAPII (2.3 μg; Stratagene) was digested with 20 units of SacI in a similar manner. The both of the SacI fragments were ligated with T4 DNA ligase and packaged in the following manner using LAMBDA INN in vitro packaging kit (Nippon Gene). To a tube containing packaging extract was added 1 μl (0.1 μg) λZAPII phage DNA and the mixture was incubated at 22° C. for 2 hours. After addition of 500 μl of SM buffer (0.58% NaCl, 0.2% MgSO$_4$·7H$_2$O, 50 mM Tris-HCl (pH 7.5), 0.01% gelatin), the mixture was gently mixed and a drop of chloroform was added to obtain a phage solution. E. coli strain XL1-Blue was inoculated into 5 ml LB medium containing 0.2% maltose and 10 mM MgSO$_4$ and incubated overnight. One milliliter each of the culture broth was charged in an Eppendorf tube and centrifuged at 3,000 rpm for 7 minutes. The supernatant was discarded and the cell pellet was suspended into 200–300 μl of 10 mM MgSO$_4$. An aliquot (100 μl) of the cell suspension was charged in a tube for phage infection. The cell suspension was incubated with 10 μl of phage solution diluted with SM buffer at 37° C. for 20 minutes. The infected bacteria were inoculated into a mixture prepared by adding 50 μl each of 0.5M isopropyl-β-thiogalactopyranoside (IPTG) and 125 μg/ml 5-bromo-4-chloro-3-indolyl-β-D-galactoside (X-gal) to 3 ml of NZY upper-layer agarose medium (1% NZ amine (casein enzymatic hydrolysate), 0.5% NaCl, 0.5% yeast extract, 0.2% $MgSO_4·7H_2O$, 0.7% agarose, pH 7.5) which was previously warmed and maintained at 48° C., and then the mixture was overlaid on NZY agarose medium (1% NZ amine (casein enzymatic hydrolysate), 0.5% NaCl, 0.5% yeast extract, 0.2% $MgSO_4·7H_2O$, 1.5% agarose, pH 7.5). Incubation was carried out at 37° C. for 6–7 hours after the medium surface dried to form plaques.

Plaque hybridization was carried out according to the method of Benton, W. D. and Davis, A. W., Science, 196, 180–182 (1977). Plaques formed on a plate were transferred onto Hybond N+ nylon membrane, and DNA derived from plaque was immobilized on the membrane with 0.4N NaOH, hybridized with previously prepared probes, and followd by autoradiography. As a result, two positive clones were obtained. The recombinant phage DNAs each containing cloned DNA fragment were purified according to the method of Yamamoto et al., Virology, 40, 734 (1970). Restriction endnuclease analysis of the DNA inserts in the positive clones revealed that the both clones have the same 2.6 kbp SacI fragment.

4. Construction of Cloning Vector

Cloning vector pUC118 (3 μg) was digested with 20 units of restriction endonuclease SacI and ligated to 2.6 kbp SacI fragment obtained in step 3 above with 1000 units of T4 DNA ligase to yield plasmids named pYH1 and pYH2.

The plasmids pYH1 and pYH2 were used to transform E. coli strain MV1184. The transformants were grown and analyzed for the expression of L-methionine γ-lyase activity.

E. coli strain MV1184 transformed with either plasmid was incubated in L-broth containing 50 μg/ml ampicillin and 1 mM IPTG at 37° C. for 17 hours. From cells was prepared 2.5 ml of cell-free extract according to the method of Nakayama, T. et al, Anal. Biochem., 138, 421–424 (1984) and subjected to an enzyme assay. The assay was carried out using an assay system containing 200 μmol of potassium phosphate buffer (pH 8.0), 40 μmol of L-methionine, 0.04 μmol of pyridoxal 5'-phosphorate and cell-free extract in a final volume of 1.6 ml. After incubating the mixture at 37° C. for 5 minutes, 0.2 ml of 50% trichloroacetic acid was added to terminate the reaction. The reaction mixture was centrifuged and the reaction product α-ketobutyrate in the supernatant was determined using 3-methyl-2-benzothiazolinone hydrazone according to the method of Soda, K., Anal. Biochem., 25, 228–235 (1968). The protein was determined according to the method of Lowry et al., J. Biol. Chem., 193, 265–275 (1951) using bovine serum albumin as a standard.

The assay revealed that the cell extract from E. coli transformants harboring plasmid pYH1 has L-methionine γ-lyase activity while that obtained from transformants harboring plasmid pYH2 does not have the activity at all as shown in Table 1 below. The results showed that the plasmids pYH1 and pYH2 differ from each other in the orientation of inserted SacI fragment. That is, the insert is in the same or reverse orientation with respect to lac promoter in pUC118.

Example 3

DNA Sequence Analysis

The plasmid pYH1 prepared in Example 2 was used for DNA sequence analysis to determine the base sequence of a DNA region encoding L-methionine γ-lyase and its flanking regions.

DNA fragments corresponding to each region to be sequenced were obtained from plasmid pYH1 and subcloned into vector pUC118 or pUC119. By means of infection of helper phage M13KO7, each single-stranded DNA was prepared according to the method of Viera et al., Methods Enzymol., 153, 3–11 (1987). The sequencing was carried out using the single-stranded DNA as a template, M13 sequence primer labeled with [γ-$^{32}$P]ATP (220 TBq/mmol: NEN Research Products) and BcaBEST sequencing kit (Takara Shuzo) by the dideoxy chain termination method. The determined base sequence is provided in SEQ ID NO: 1, which contains one open reading frame of 1194 nuclotides in total length starting with ATG at positions 61–63. This region encodes a protein of 398 amino acid residues and was identified as structural gene of L-methionine γ-lyase on the basis of the facts below.

a) The N-terminal amino acid sequence is in agreement with that of previously determined sequence of L-methionine γ-lyase (Nakayama, T. et al., Biochemistry, 27, 1587–1591 (1988));

b) the presumed amino acid composition of the protein enencoded is in good agreement with that of L-methionine γ-lyase (Nakayama, T. et al., ibid.); and c) the calculated molecular weight (about 43 kDa) is in agreement with that of L-methionine γ-lyase subunit (Nakayama, T. et al., Anal. Biochem., 138, 421–424 (1984)).

Example 4

Construction of Expression Vector

Recombinant E. coli MV1184/pYH1, when grown in L-broth while adding IPTG at a final concentration of 1 mM, expressed L-methionine γ-lyase efficiently. An expression vector capable of directing higher expression in E. coli was constructed as follows.

A 1.5 kb SalI fragment was isolated by partially digesting 20 μg of pYH2 with 10 U of SalI. The 1.5 kb SalI fragment was then ligated to a 3.14 kb fragment obtained by digesting 3 μg of pUC119 (Takara Shuzo) with 20 U of SalI in the presence of 1000 U of T4 DNA ligase to yield pYH101. The pYH101 (2 μg) was digested with 200 U of HindIII to obtain a 4.5 kb fragment, which was then self-ligated with 1000 U of T4 DNA ligase and transformed into E. coli strain MV1184. Transformants were selected by incubating on L-agar containing 50 μg/ml ampicillin overnight at 37° C. A recombinant plasmid named pYH103 was isolated from the intended transformant. FIG. 2 shows the restriction enzyme cleavage map of plasmid pYH103.

The plasmid pYH103 was subjected to the assay for the ability to direct the expression of L-methionine γ-lyase activity in a manner similar to that described in Example 2, step 4 above. The results are summarized in Table 1 below.

TABLE 1

|  | Specific Activity (U/mg protein) | |
| --- | --- | --- |
|  | LB | LB (IPTG) |
| pYH1 | 0.008 | 0.39 |
| PYH2 | NA | — |
| pYH103 | — | 0.71 |

Note:
One unit of the enzyme is defined as the amount of enzyme that catalyzes the formation of 1 μmol of α-ketobutyrate at 37° C. per minute.
LB means L-broth and LB (IPTG) means L-broth containing 1 mM IPTG.
"NA" and "—" mean "no activity" and "not assayed", respectively.

Example 5

Construction of Plasmid with High Expression Efficiency

Plasmid pYH103 (5 μg) prepared in Example 4 was digested with 30 units of HindIII restriction endonuclease and precipitated with ethanol, which was followed by digestion with 30 units of BamHI. After agarose gel electrophoresis, a 1.3 kbp HindIII-BamHI fragment containing the structural gene of L-methionine γ-lyase was extracted from the gel and purified, and dissolved in 20 μl TE buffer (10 mM Tris-HCl (pH 7.5), 1 mM EDTA (pH 8.0)). The resultant fragment was then blunt-ended by the addition of 2 units of Klenow enzyme (Nippon Gene).

Figure 3:
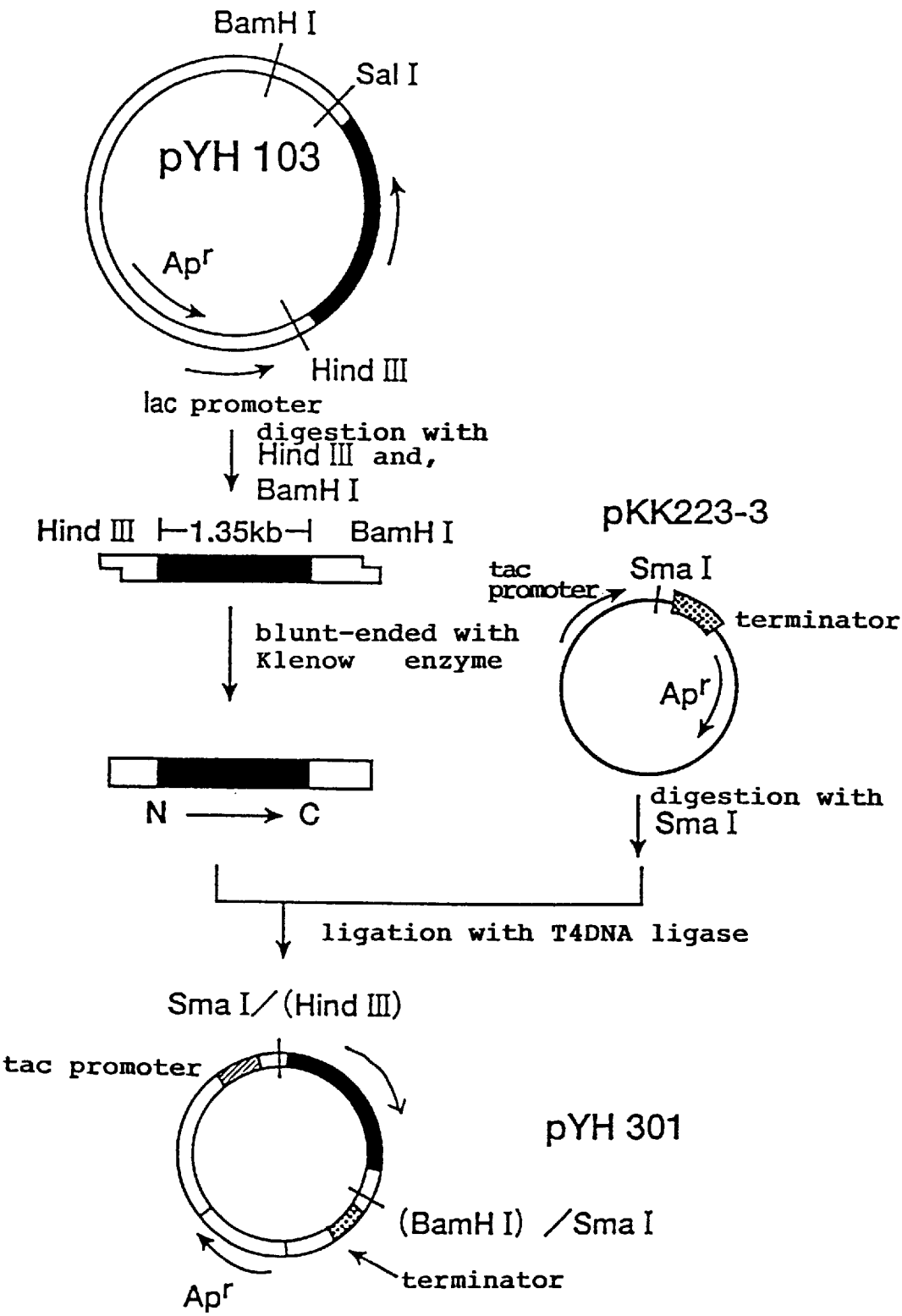
FIG. 3 is a flow chart illustrating the procedures for constructing the expression plasmid pYH301.

Plasmid pKK223-3 (3 μg, Pharmacia Biotech) was digested with 30 units of restriction endonuclease SmaI. To the reaction solution (3 μl), the solution (10 μl) containing the blunt-ended fragment above and 1000 units of T4 DNA ligase were added and incubated for ligation to obtain plasmid pYH301. The restriction enzyme cleavage map of the resultant plasmid pYH301 is provided in FIG. 3.

The plasmid pYH301 was assayed to evaluate the expression efficiency according to the method described in Example 2, step 4 except that E. coli strain JM109 (Takara Shuzo) was used as a host cell. The assay revealed that a cell free extract obtained from the transformant harboring plasmid pYH301 grown in L-broth containing 1 mM IPTG at 37° C. for 17 hours shows a specific activity of 0.82 U/mg.

What is claimed is:

1. A recombinant protein comprising an amino acid sequence of residue from No. 2 to residue No. 398 of SEQ ID NO:1, wherein said protein is free of other proteins from P. putida or a variant thereof.

2. The recombinant protein as claimed in claim 1, wherein the amino acid sequence further contains a methionine residue attached at its N-terminus.

3. The recombinant protein as claimed in claim 1 or 2, wherein the amino acid sequence is encoded by DNA originated from a strain of Pseudomonas putida.

4. The recombinant protein as claimed in claim 1 or 2, wherein the amino acid sequence is encoded by DNA originated from Pseudomonas putida ICR3460 (FERM BP-5238).

5. An oligomeric enzyme comprising as subunit the recombinant proteins as claimed in claim 1 or 2.

6. The enzyme as claimed in claim 5, which is a tetramer.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 1320 base pairs
    ( B ) TYPE: nucleic acid
    ( C ) STRANDEDNESS: double
    ( D ) TOPOLOGY: linear ( i i ) MOLECULE TYPE: other nucleic acid ( i x ) FEATURE:
    ( A ) NAME/KEY: CDS
    ( B ) LOCATION: 61..1254

( x i ) SEQUENCE DESCRIPTION: SEQ ID NO:1:

```
TGGAAAAATT  TAAGCCGGTC  TGTGGAATAA  GCTTATAACA  AACCACAAGA  GGCGGTTGCC           60

ATG  CAC  GGC  TCC  AAC  AAG  CTC  CCA  GGA  TTT  GCC  ACC  CGC  GCC  ATT  CAC          108
Met  His  Gly  Ser  Asn  Lys  Leu  Pro  Gly  Phe  Ala  Thr  Arg  Ala  Ile  His
 1              5                        10                       15

CAT  GGC  TAC  GAC  CCC  CAG  GAC  CAC  GGC  GGC  GCA  CTG  GTG  CCA  CCG  GTC          156
His  Gly  Tyr  Asp  Pro  Gln  Asp  His  Gly  Gly  Ala  Leu  Val  Pro  Pro  Val
                  20                       25                       30

TAC  CAG  ACC  GCG  ACG  TTC  ACC  TTC  CCC  ACC  GTG  GAA  TAC  GGC  GCT  GCG          204
Tyr  Gln  Thr  Ala  Thr  Phe  Thr  Phe  Pro  Thr  Val  Glu  Tyr  Gly  Ala  Ala
         35                       40                       45

TGC  TTT  GCC  GGC  GAG  CAG  GCC  GGG  CAT  TTC  TAC  AGC  CGC  ATC  TCC  AAC          252
Cys  Phe  Ala  Gly  Glu  Gln  Ala  Gly  His  Phe  Tyr  Ser  Arg  Ile  Ser  Asn
         50                       55                       60

CCC  ACC  CTC  AAC  CTG  CTG  GAA  GCA  CGC  ATG  GCC  TCG  CTG  GAA  GGC  GGC          300
Pro  Thr  Leu  Asn  Leu  Leu  Glu  Ala  Arg  Met  Ala  Ser  Leu  Glu  Gly  Gly
 65                       70                       75                       80

GAG  GCC  GGG  CTG  GCG  CTG  GCC  TCG  GGC  ATG  GGG  GCG  ATC  ACG  TCC  ACG          348
Glu  Ala  Gly  Leu  Ala  Leu  Ala  Ser  Gly  Met  Gly  Ala  Ile  Thr  Ser  Thr
                  85                       90                       95

CTA  TGG  ACA  CTG  CTG  CGC  CCC  GGT  GAC  GAG  GTG  CTG  CTG  GGC  AAC  ACC          396
Leu  Trp  Thr  Leu  Leu  Arg  Pro  Gly  Asp  Glu  Val  Leu  Leu  Gly  Asn  Thr
                 100                      105                      110
```

| | | | | | | | | | | | | | | | | |
|---|---|---|---|---|---|---|---|---|---|---|---|---|---|---|---|---|
| CTG | TAC | GGC | TGC | ACC | TTT | GCC | TTC | CTG | CAC | CAC | GGC | ATC | GGC | GAG | TTC | 444 |
| Leu | Tyr | Gly | Cys | Thr | Phe | Ala | Phe | Leu | His | His | Gly | Ile | Gly | Glu | Phe | |
| | | 115 | | | | | 120 | | | | | 125 | | | | |
| GGG | GTC | AAG | CTG | CGC | CAT | GTG | GAC | ATG | GCC | GAC | CTG | CAG | GCA | CTG | GAG | 492 |
| Gly | Val | Lys | Leu | Arg | His | Val | Asp | Met | Ala | Asp | Leu | Gln | Ala | Leu | Glu | |
| | 130 | | | | | 135 | | | | | 140 | | | | | |
| GCG | GCC | ATG | ACG | CCG | GCC | ACC | CGG | GTG | ATC | TAT | TTC | GAG | TCG | CCG | GCC | 540 |
| Ala | Ala | Met | Thr | Pro | Ala | Thr | Arg | Val | Ile | Tyr | Phe | Glu | Ser | Pro | Ala | |
| 145 | | | | | 150 | | | | | 155 | | | | | 160 | |
| AAC | CCC | AAC | ATG | CAC | ATG | GCC | GAT | ATC | GCC | GGC | GTG | GCG | AAG | ATT | GCA | 588 |
| Asn | Pro | Asn | Met | His | Met | Ala | Asp | Ile | Ala | Gly | Val | Ala | Lys | Ile | Ala | |
| | | | | 165 | | | | | 170 | | | | | 175 | | |
| CGC | AAG | CAC | GGC | GCG | ACC | GTG | GTG | GTC | GAC | AAC | ACC | TAC | TGC | ACG | CCG | 636 |
| Arg | Lys | His | Gly | Ala | Thr | Val | Val | Val | Asp | Asn | Thr | Tyr | Cys | Thr | Pro | |
| | | | 180 | | | | | 185 | | | | | 190 | | | |
| TAC | CTG | CAA | CGG | CCA | CTG | GAG | CTG | GGC | GCC | GAC | CTG | GTG | GTG | CAT | TCG | 684 |
| Tyr | Leu | Gln | Arg | Pro | Leu | Glu | Leu | Gly | Ala | Asp | Leu | Val | Val | His | Ser | |
| | | 195 | | | | | 200 | | | | | 205 | | | | |
| GCC | ACC | AAG | TAC | CTG | AGC | GGC | CAT | GGC | GAC | ATC | ACT | GCT | GGC | ATT | GTG | 732 |
| Ala | Thr | Lys | Tyr | Leu | Ser | Gly | His | Gly | Asp | Ile | Thr | Ala | Gly | Ile | Val | |
| | | 210 | | | | | 215 | | | | | 220 | | | | |
| GTG | GGC | AGC | CAG | GCA | CTG | GTG | GAC | CGT | ATA | CGT | CTG | CAG | GGC | CTC | AAG | 780 |
| Val | Gly | Ser | Gln | Ala | Leu | Val | Asp | Arg | Ile | Arg | Leu | Gln | Gly | Leu | Lys | |
| 225 | | | | | 230 | | | | | 235 | | | | | 240 | |
| GAC | ATG | ACC | GGT | GCG | GTG | CTC | TCG | CCC | CAT | GAC | GCC | GCA | CTG | TTG | ATG | 828 |
| Asp | Met | Thr | Gly | Ala | Val | Leu | Ser | Pro | His | Asp | Ala | Ala | Leu | Leu | Met | |
| | | | | 245 | | | | | 250 | | | | | 255 | | |
| CGC | GGC | ATC | AAG | ACC | CTC | AAC | CTG | CGC | ATG | GAC | CGC | CAC | TGC | GCC | AAC | 876 |
| Arg | Gly | Ile | Lys | Thr | Leu | Asn | Leu | Arg | Met | Asp | Arg | His | Cys | Ala | Asn | |
| | | | 260 | | | | | 265 | | | | | 270 | | | |
| GCT | CAG | GTG | CTG | GCC | GAG | TTC | CTC | GCC | CGG | CAG | CCG | CAG | GTG | GAG | CTG | 924 |
| Ala | Gln | Val | Leu | Ala | Glu | Phe | Leu | Ala | Arg | Gln | Pro | Gln | Val | Glu | Leu | |
| | | 275 | | | | | 280 | | | | | 285 | | | | |
| ATC | CAT | TAC | CCG | GGC | CTG | GCG | AGC | TTC | CCG | CAG | TAC | ACC | CTG | GCC | CGC | 972 |
| Ile | His | Tyr | Pro | Gly | Leu | Ala | Ser | Phe | Pro | Gln | Tyr | Thr | Leu | Ala | Arg | |
| | 290 | | | | | 295 | | | | | 300 | | | | | |
| CAG | CAG | ATG | AGC | CAG | CCG | GGC | GGC | ATG | ATC | GCC | TTC | GAA | CTC | AAG | GGC | 1020 |
| Gln | Gln | Met | Ser | Gln | Pro | Gly | Gly | Met | Ile | Ala | Phe | Glu | Leu | Lys | Gly | |
| 305 | | | | | 310 | | | | | 315 | | | | | 320 | |
| GGC | ATC | GGT | GCC | GGG | CGG | CGG | TTC | ATG | AAC | GCC | CTG | CAA | CTG | TTC | AGC | 1068 |
| Gly | Ile | Gly | Ala | Gly | Arg | Arg | Phe | Met | Asn | Ala | Leu | Gln | Leu | Phe | Ser | |
| | | | | 325 | | | | | 330 | | | | | 335 | | |
| CGC | GCG | GTG | AGC | CTG | GGC | GAT | GCC | GAG | TCG | CTG | GCG | CAG | CAC | CCG | GCA | 1116 |
| Arg | Ala | Val | Ser | Leu | Gly | Asp | Ala | Glu | Ser | Leu | Ala | Gln | His | Pro | Ala | |
| | | | 340 | | | | | 345 | | | | | 350 | | | |
| AGC | ATG | ACT | CAT | TCC | AGC | TAT | ACC | CCA | GAG | GAG | CGT | GCG | CAT | TAC | GGC | 1164 |
| Ser | Met | Thr | His | Ser | Ser | Tyr | Thr | Pro | Glu | Glu | Arg | Ala | His | Tyr | Gly | |
| | | 355 | | | | | 360 | | | | | 365 | | | | |
| ATC | TCC | GAG | GGG | CTG | GTG | CGG | TTG | TCG | GTG | GGG | CTG | GAA | GAC | ATC | GAC | 1212 |
| Ile | Ser | Glu | Gly | Leu | Val | Arg | Leu | Ser | Val | Gly | Leu | Glu | Asp | Ile | Asp | |
| | 370 | | | | | 375 | | | | | 380 | | | | | |
| GAC | CTG | CTG | GCC | GAT | GTG | CAA | CAG | GCA | CTC | AAG | GCG | AGT | GCC | | | 1254 |
| Asp | Leu | Leu | Ala | Asp | Val | Gln | Gln | Ala | Leu | Lys | Ala | Ser | Ala | | | |
| 385 | | | | | 390 | | | | | 395 | | | | | | |

TGAACCCGTC ACGGATGAGG TCAATGCAAT GGTGGCAATG ATGAACTTG TGCCTGGCGA    1314

CGGCGT    1320

( 2 ) INFORMATION FOR SEQ ID NO:2:

( i ) SEQUENCE CHARACTERISTICS:

(A) LENGTH: 398 amino acids
(B) TYPE: amino acid
(D) TOPOLOGY: linear (ii) MOLECULE TYPE: protein (xi) SEQUENCE DESCRIPTION: SEQ ID NO:2:

| Met | His | Gly | Ser | Asn | Lys | Leu | Pro | Gly | Phe | Ala | Thr | Arg | Ala | Ile | His |
|---|---|---|---|---|---|---|---|---|---|---|---|---|---|---|---|
| 1 | | | | 5 | | | | | 10 | | | | | 15 | |
| His | Gly | Tyr | Asp | Pro | Gln | Asp | His | Gly | Gly | Ala | Leu | Val | Pro | Pro | Val |
| | | | 20 | | | | | 25 | | | | | 30 | | |
| Tyr | Gln | Thr | Ala | Thr | Phe | Thr | Phe | Pro | Thr | Val | Glu | Tyr | Gly | Ala | Ala |
| | | | 35 | | | | 40 | | | | | 45 | | | |
| Cys | Phe | Ala | Gly | Glu | Gln | Ala | Gly | His | Phe | Tyr | Ser | Arg | Ile | Ser | Asn |
| | | 50 | | | | | 55 | | | | | 60 | | | |
| Pro | Thr | Leu | Asn | Leu | Leu | Glu | Ala | Arg | Met | Ala | Ser | Leu | Glu | Gly | Gly |
| 65 | | | | | 70 | | | | | 75 | | | | | 80 |
| Glu | Ala | Gly | Leu | Ala | Leu | Ala | Ser | Gly | Met | Gly | Ala | Ile | Thr | Ser | Thr |
| | | | | 85 | | | | | 90 | | | | | 95 | |
| Leu | Trp | Thr | Leu | Leu | Arg | Pro | Gly | Asp | Glu | Val | Leu | Leu | Gly | Asn | Thr |
| | | | 100 | | | | | 105 | | | | | 110 | | |
| Leu | Tyr | Gly | Cys | Thr | Phe | Ala | Phe | Leu | His | His | Gly | Ile | Gly | Glu | Phe |
| | | | 115 | | | | 120 | | | | | 125 | | | |
| Gly | Val | Lys | Leu | Arg | His | Val | Asp | Met | Ala | Asp | Leu | Gln | Ala | Leu | Glu |
| | | 130 | | | | | 135 | | | | | 140 | | | |
| Ala | Ala | Met | Thr | Pro | Ala | Thr | Arg | Val | Ile | Tyr | Phe | Glu | Ser | Pro | Ala |
| 145 | | | | | 150 | | | | | 155 | | | | | 160 |
| Asn | Pro | Asn | Met | His | Met | Ala | Asp | Ile | Ala | Gly | Val | Ala | Lys | Ile | Ala |
| | | | | 165 | | | | | 170 | | | | | 175 | |
| Arg | Lys | His | Gly | Ala | Thr | Val | Val | Val | Asp | Asn | Thr | Tyr | Cys | Thr | Pro |
| | | | 180 | | | | | 185 | | | | | 190 | | |
| Tyr | Leu | Gln | Arg | Pro | Leu | Glu | Leu | Gly | Ala | Asp | Leu | Val | Val | His | Ser |
| | | | 195 | | | | 200 | | | | | 205 | | | |
| Ala | Thr | Lys | Tyr | Leu | Ser | Gly | His | Gly | Asp | Ile | Thr | Ala | Gly | Ile | Val |
| | 210 | | | | | 215 | | | | | 220 | | | | |
| Val | Gly | Ser | Gln | Ala | Leu | Val | Asp | Arg | Ile | Arg | Leu | Gln | Gly | Leu | Lys |
| 225 | | | | | 230 | | | | | 235 | | | | | 240 |
| Asp | Met | Thr | Gly | Ala | Val | Leu | Ser | Pro | His | Asp | Ala | Ala | Leu | Leu | Met |
| | | | | 245 | | | | | 250 | | | | | 255 | |
| Arg | Gly | Ile | Lys | Thr | Leu | Asn | Leu | Arg | Met | Asp | Arg | His | Cys | Ala | Asn |
| | | | 260 | | | | | 265 | | | | | 270 | | |
| Ala | Gln | Val | Leu | Ala | Glu | Phe | Leu | Ala | Arg | Gln | Pro | Gln | Val | Glu | Leu |
| | | 275 | | | | | 280 | | | | | 285 | | | |
| Ile | His | Tyr | Pro | Gly | Leu | Ala | Ser | Phe | Pro | Gln | Tyr | Thr | Leu | Ala | Arg |
| | 290 | | | | | 295 | | | | | 300 | | | | |
| Gln | Gln | Met | Ser | Gln | Pro | Gly | Gly | Met | Ile | Ala | Phe | Glu | Leu | Lys | Gly |
| 305 | | | | | 310 | | | | | 315 | | | | | 320 |
| Gly | Ile | Gly | Ala | Gly | Arg | Arg | Phe | Met | Asn | Ala | Leu | Gln | Leu | Phe | Ser |
| | | | | 325 | | | | | 330 | | | | | 335 | |
| Arg | Ala | Val | Ser | Leu | Gly | Asp | Ala | Glu | Ser | Leu | Ala | Gln | His | Pro | Ala |
| | | | 340 | | | | | 345 | | | | | 350 | | |
| Ser | Met | Thr | His | Ser | Ser | Tyr | Thr | Pro | Glu | Glu | Arg | Ala | His | Tyr | Gly |
| | | | 355 | | | | | 360 | | | | | 365 | | |
| Ile | Ser | Glu | Gly | Leu | Val | Arg | Leu | Ser | Val | Gly | Leu | Glu | Asp | Ile | Asp |
| | | | 370 | | | | | 375 | | | | | 380 | | |

```
Asp  Leu  Leu  Ala  Asp  Val  Gln  Gln  Ala  Leu  Lys  Ala  Ser  Ala
385                 390                      395
```

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

```
Ile  His  His  Gly  Tyr  Asp  Pro
1                  5
```

7. A pharmaceutical composition comprising the enzyme as claimed in 5 or 6 and a pharmaceutically acceptable carrier thereof.

8. The recombinant protein as claimed in claim 1 or 2 which can be purified from cultured host cells transformed with a recombinant vector containing a nucleotide sequence from No. 61 or 64 to No. 1254 of that shown in SEQ ID NO:1, or a nucleotide sequence which hybridizes under stringent conditions to the nucleotide sequence from No. 61 or 64 to No. 1254 of that shown in SEQ ID NO:1.

9. An anti-tumor agent which comprises the enzyme as claimed in claim 6.

* * * * *